Figure 19:
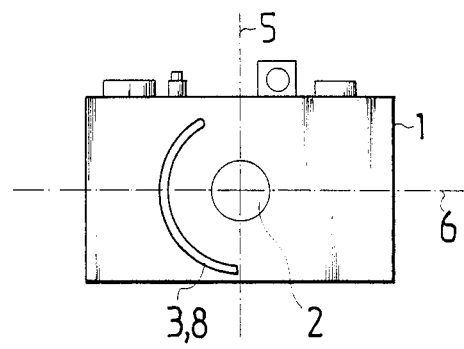

United States Patent [19]

Kaakinen

[11] Patent Number: 4,523,820
[45] Date of Patent: Jun. 18, 1985

[54] PROCEDURE AND MEANS FOR ESTABLISHING AND RECORDING ERRORS OF THE EYE

[76] Inventor: Kari A. Kaakinen, Karankakatu 15, SF-87500 Kajaani 50, Finland

[21] Appl. No.: 377,520

[22] Filed: May 12, 1982

[30] Foreign Application Priority Data

May 19, 1981 [FI] Finland ................. 811541

[51] Int. Cl.³ .................... G03B 29/00; A64B 3/14
[52] U.S. Cl. ................................ 351/206; 354/62
[58] Field of Search ............ 351/206, 207, 208, 221; 354/62

[56] References Cited

U.S. PATENT DOCUMENTS 4,259,948 4/1981 Urban ...................... 351/206 X

Primary Examiner—Rodney B. Bovernick
Attorney, Agent, or Firm—Neuman, Williams, Anderson & Olson

[57] ABSTRACT

A procedure and means for establishing and recording errors of the eye, the eye being illuminated with the aid of a flash-light (3) placed eccentrically with reference to the objective (2) of the camera (1). The cornea and retina are photographed simultaneously in at least two different meridians (5, 6) of the eye in order to elicit and record the retinal reflections and corneal reflections occurring in these. The apparatus comprises members for the simultaneous photographing of the eye in two different meridians of the eye, for instance a camera provided with an objective (2) and with two point lights (3, 4) disposed in different meridians of the objective, or with one flash-light (3) and two objectives (2, 2') placed in different meridians of the latter.

7 Claims, 20 Drawing Figures

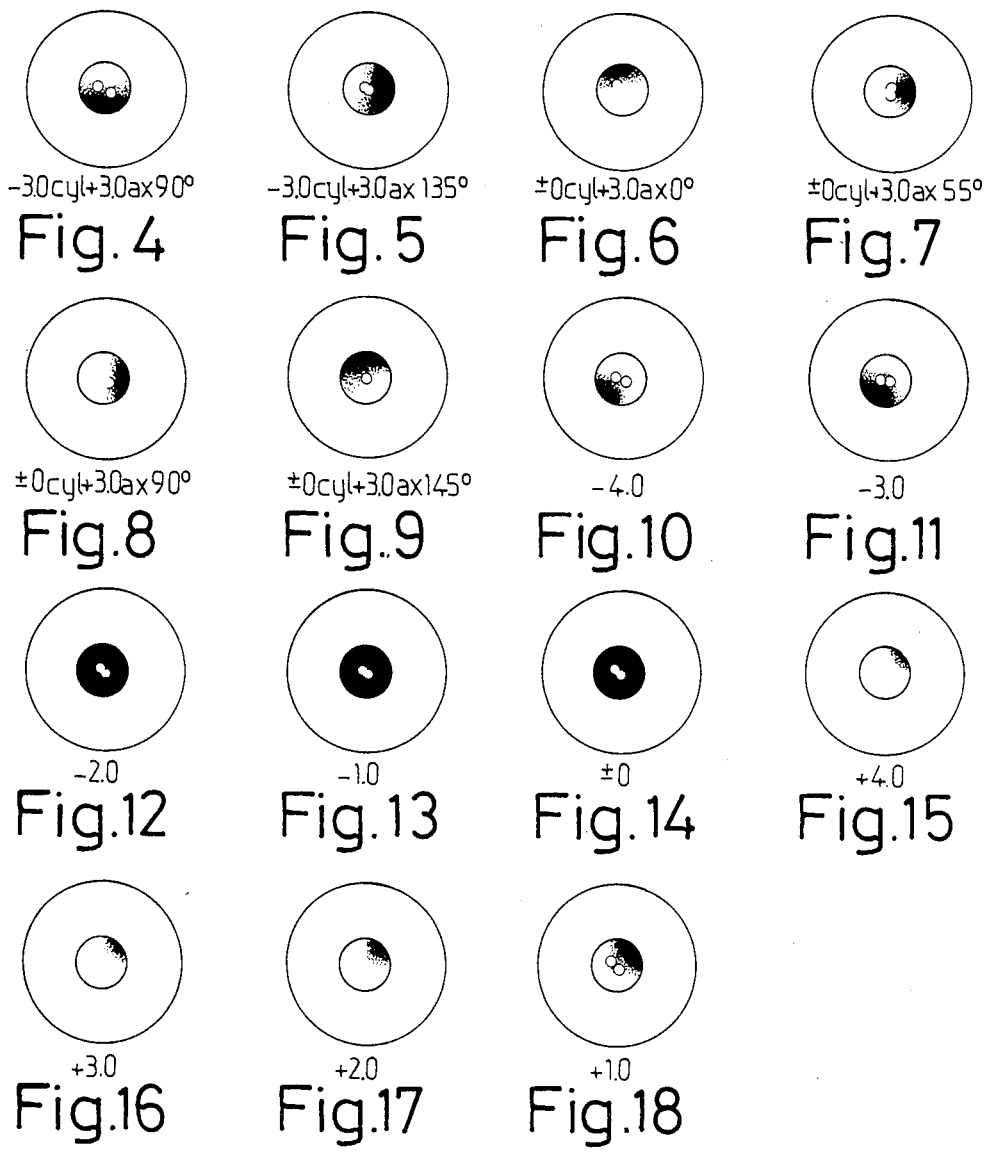

PROCEDURE AND MEANS FOR ESTABLISHING AND RECORDING ERRORS OF THE EYE

The present invention concerns a procedure to be applied in static skiascopy to the purpose of establishing and recording errors of the eye in patients with the aid of photography, whereat for illuminating the eye is used a flash-light eccentrically disposed with reference to the camera objective. The invention further concerns a means for carrying out the procedure, said means comprising a camera provided with an objective and a flash-light which is eccentrically disposed with reference to the objective.

In the art no fully satisfactory procedure is known for the screening and finding among an extensive series of patients, by utilizing photography and on the basis of photographic material, of errors of the eye, strabismus and in particular anisometropia. Further, no procedures are known for photographing the eye and the red reflection for measurements of refraction.

The object of the present invention is to eliminate the drawbacks mentioned. It is particularly an object: to provide a procedure, usable in static skiascopy, for photographing the eye and the red reflection to the purpose of establishing and recording the errors of the eye. It is still another object: to provide a photographic procedure, more uncomplicated and versatile than any methods of prior art, for establishing and recording the refractive errors occurring in different meridians of the eye. It is furthermore an object of the invention: to further develop the procedure based on photography in such a way that it is applicable in accurate refraction measurements on the eye on the basis of photographic material.

It is furthermore an object of the invention to provide a means for carrying out the procedure.

Regarding the features which are characteristic of the invention, reference is made to the claims section.

The invention is based on photographing the eye, that is the cornea, cornea reflections and retinal reflections, simultaneously in at least two different meridians of the eye. The procedure may be carried out in that the eye is illuminated in the direction of at least two meridians when photographing it through an objective lens; the illumination then takes place from at least two points located eccentrically with reference to the objective and in different meridians of the objective. The procedure may also be carried out by photographing the eye simultaneously with reference to this point light used for illumination in the direction of two meridians; in that case the eye is photographed with regard to this point light used for illumination eccentrically and through objectives placed in different medians with reference to the point light. When using one point light and two point objectives placed eccentrically with reference thereto, naturally two images are obtained of the eye under examination; in contrast when one objective and two point lights placed eccentrically thereto are used, only one image is obtained of the eye under examination, and this further simplifies the evaluation of the results.

In the procedure of the invention, the illumination eccentric to the objective causes a retinal reflection, the so-called red reflection, in which for instance the potential refractive errors, the colour substance changes and other red reflection changes in the eye become apparent.

Both of the eyes may be photographed at one time, even many people, for example a school class, may be photographed at one time.

The measuring of refractive errors is based on separate rays or beams emitted from the point of observation, i.e. from the centre of the objective eccentrically and concentrically from the periphery of the objective and which are reflected by the retina of each eye. The assessment of strabismus or orthocularity is based on the location of the corneal reflections; the reflections are then visible in one and the same photograph.

In connection with photography the eye is illuminated, according to the invention, in at least two main meridians of the eye, for instance in the horizontal and vertical meridian simultaneously, possibly in several meridians as well. It is also possible to use in the procedure a peripheral flash-light eccentric with regard to the camera objective, e.g. a ring flash-light which has been partially covered over.

The invention is based on the unexpected and novel observation, and which differs from earlier results, that by illuminating the eye simultaneously from at least two points placed coaxially and eccentrically with reference to the objective lens it becomes possible to reproduce an image of the eye, simultaneously and in one photograph, in two different meridians in respect of the changes in the retinal reflections and in the refractive errors. Particularly that is novel that the light from two different points and the diffuse light do not interfere with or impede the observations, instead of which the refractive changes are simultaneously detected in at least two different meridians. The refractive errors may also appear from the two meridians as superimposed on each other, but this does not interfere with their observing as a rule.

As set forth in the foregoing, it is possible to use instead of one objective and two point lights placed eccentrically with reference thereto, one point light and two objectives placed eccentrically thereto.

The invention possesses quite essential significance in establishing and recording errors of the eye and in screening errors. In earlier practice, the results have implied diagnostic examination of the patient in person; this has been exceedingly cumbersome, laborious and even outright impossible in the case of infants. It is now possible to carry out equivalent examinations by photographing the patients' eyes and performing screening of the results and also a more profound examination on the basis of the photographic series. It should further be noted in assessing the usability of this procedure that the photographing of the eye, when applying the method of examination of the invention, may be carried out from a distance, e.g. from 1-2-3 m distance, whereby therefore the procedure is especially well-adapted also for ocular examinations of timid patients, such as children or even infants as young as one year old.

Figure 20:
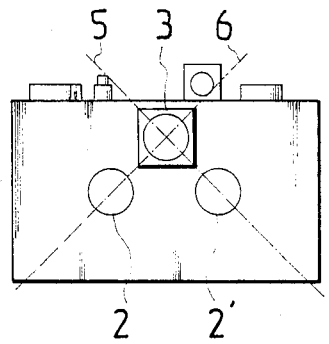

The invention is described in detail in the following, with the aid of embodiment examples and results of experiment, reference being made to the accompanying drawings, wherein:

FIG. 1 presents, viewed from the front, a means according to the invention for establishing errors of the eye, FIGS. 2-18 show photographic images of a test eye, where various refractive errors occurring in eyes have been set, FIG. 19 presents another means for establishing and recording errors of the eye, and FIG. 20 presents a third means according to the invention for establishing and recording errors of the eye.

EXAMPLE 1

In a study the refractive errors of the eye were observed, using as demonstration means an optic test eye by Carl Zeiss, Jena, this test eye being photographed with different refractive errors as taught by the invention. The photography was done using a camera 1, FIG. 1, Canon F-1 fitted with an objective lens 2, Canon FT 100 mm 1:2.8 S.S.C., and with two flash-light units 3 and 4 placed with reference to the objective concentrically and eccentrically, and symmetrically and radially, flash-lights Popular V 1, the reflectors of the flash-lights being located, one in the vertical plane passing through the optical axis 7 of the objective and the other on the right, in the horizontal plane passing through the objective, whereby the sides of the flash-light reflectors closest to the optical axis had 15 mm distance therefrom; the photographs were made using colour film 100 ASA. The flash-light units had been arranged to operate in synchronism, exposure time 1/60 second, stop 8, distance 1 m. The results are seen in FIGS. 2–18. The refractive errors of the test eye are clearly evident in the picture series if one compares this with the refractive errors inscribed in the compilation of photographs.

EXAMPLE 2

Photography of the test eye as in Example 1 was repeated, using the same camera provided with an annular flash-light unit Sunpak Gx 17 placed concentrically with reference to the objective, the lowest about 120-degree sector of this unit being covered in order to produce eccentricity. The camera distance was 2 m, stop 2.8, colour film 200 ASA; the experimental set-up was in other respects the same as in Example 1. The photograph series hereby obtained revealed the refractive errors of the test eye similarly as in Example 1, refractive errors being observable about 10% less strongly.

The camera 1 for carrying out the procedure of the invention, depicted in FIG. 19, comprises an objective 2 and a flash-light 3. The flash-light has been placed concentrically with the objective 2 and eccentrically, and it consists of a ring flash-light unit 8 consisting of a part of a ring. The light generated at photographing in the ring flash-light unit is equivalent to the light emitted by a plurality of point lights arranged in annular configuration. The meridians 5, 6 of the objective 2 positioned at right angles to each other are seen in FIG. 19.

The camera according to another embodiment of the invention, depicted in FIG. 20, comprises one flash-light unit 3 and two objectives 2, 2' placed eccentrically with reference to the flash-light and concentrically, i.e. in different meridians 5, 6 with reference to the flash-light and to the eye that is being photographed. When using this means, two images are obtained with it, which reveal the errors of the eye in the respective meridians.

Clinical examinations that have been performed have shown that the procedure and means of the invention are excellently appropriate for use in establishing strabismus, anisometropia and refractive errors. Moreover, when the patient's both eyes and their surroundings are photographed simultaneously, the procedure has great significance on the whole in examining and recording the state and errors of the eyes and of their surroundings and in screening the material gained in such study. Simultaneous examination in both eyes, or in one eye only, of the light-refracting media, for instance of clouded spots and of the central retina reflecting the rays is based in this method on changes in reflectivity and on the behaviour of the reflected beams in the media mentioned. These phenomena are recordable, as taught by the invention, by photographing from a point of observation on which the examinee's gaze is trained.

In addition to screening studies of infants, the procedure may to advantage be used also in screening the adult population and old persons. In addition to the errors of the eye which have been referred to, the procedure gives a possibility to document and study other errors of the eye as well. As has been observed before, also in the retinal reflection or the so-called red reflection changes are induced by changes occurring in the central reflecting retina, for instance by inflammations, tumours etc. Furthermore, significant changes in the refractive media of the eye are made visible, as taught by the invention, in the retinal reflection that is photographed. That measurements can be made of the ocular status recorded is also an essential thing because congenital glaucoma for instance causes corneal distension, and corneal diameters surpassing a given limit are to be considered indications for additional examination.

The accuracy of the procedure with photography at 1 m distance with regard to strabismus is about 3°, deviations of ocular position amounting to 3° being clearly observable, and 2-degree changes being limit values, which usually also are revealed. Regarding refractive errors the sensitivity of the procedure depends on the point of observation/flash-light distance, that is on the distance between the centre of the lens and the reflecting margin of the flash-light lamp closest to the camera lens, and on the distance of photography and on the size of the pupil. The sensitivity of the procedure with regard to refractive errors increases as the distance of photography is increased and as the lens centre/flash-light units distance is decreased. The sensitivity of the procedure with respect to refractive errors also increases with increasing pupil size.

In the foregoing, and subsequently, the term "photography" is understood to mean not only conventional photography based on conventional visible light but also photography based on ultraviolet beams, infra-red beams and laser beams on conventional light-sensitive film and other recording of the image e.g. on magnetic tape similarly as with video apparatus. Moreover, photography is in this connection also understood to mean the storing and recording of an image of the eye and the eye fundus based on physical rays other than light rays.

In the disclosure and in the claims, "two-objectives" is understood to refer not only to two physically separate objectives but also to ancillary equipment that may be used on cameras and by which the photograph taken through one objective can be divided into two or more separate images.

The embodiment examples are intended for illustration of the invention, without in any way confining it.

I claim:

1. A method for establishing and recording errors of the eye which comprises simultaneously photographing from a distance of at least about one meter from the eye the cornea, corneal reflexes and retinal reflexes of the eye in at least two different meridians of the eye using a camera having at least one objective lens and at least one light source, the objective lens and light source being disposed in different meridians of the eye.

2. A method according to claim 1 wherein the photographing is carried out simultaneously using two objective camera lenses disposed eccentrically to a light source and in different meridians of the eye than the light source.

3. A method in accordance with claim 1 wherein the photographing is carried out simultaneously while directing light to the eye from at least two light sources disposed eccentrically with respect to the objective lens of the camera and in different meridians of the eye.

4. A method in accordance with claim 1 wherein the photographing is carried out simultaneously while directing light to the eye from at least two light sources, one light source being disposed in a plane vertical to the objective lens and another light source being disposed in a plane horizontal to the objective lens, and both light sources being disposed at a given distance from the optical axis of the objective lens of the camera.

5. A method in accordance with claim 1 wherein the photographing is carried out simultaneously by directing light to the eye from a series of light sources arranged eccentrically and annularly with respect to the objective lens of the camera.

6. A method in accordance with claim 5 wherein the series of light sources comprises a ring flash-light unit.

7. A method in accordance with claim 1 wherein the photographing is carried out simultaneously by directing light to the eye from punctiform light sources arranged eccentrically and annularly with respect to the objective lens of the camera.

* * * * *